United States Patent
Koest

(10) Patent No.: US 7,252,380 B2
(45) Date of Patent: Aug. 7, 2007

(54) OPHTHALMOLOGIC ANALYSIS SYSTEM

(75) Inventor: Gert Koest, Hannover (DE)

(73) Assignee: Oculus Optikgeraete GmBH, Westzlar Dutenhofen (DE)

( * ) Notice: Subject to any disclaimer, the term of this patent is extended or adjusted under 35 U.S.C. 154(b) by 523 days.

(21) Appl. No.: 10/933,905

(22) Filed: Sep. 2, 2004

(65) Prior Publication Data

US 2005/0057722 A1 Mar. 17, 2005

(30) Foreign Application Priority Data

Sep. 2, 2003 (DE) .......................... 203 13 745 U

(51) Int. Cl.
*A61B 3/10* (2006.01)
*A61B 3/14* (2006.01)

(52) U.S. Cl. ...................... 351/205; 351/209

(58) Field of Classification Search ......... 351/200–223
See application file for complete search history.

(56) References Cited

U.S. PATENT DOCUMENTS

| | | | |
|---|---|---|---|
| 6,419,361 B2* | 7/2002 | Cabib et al. ................. | 351/221 |
| 6,428,168 B2 | 8/2002 | Sarver et al. ................ | 351/212 |
| 6,779,891 B1 | 8/2004 | Barth et al. .................. | 351/212 |
| 2002/0154269 A1 | 10/2002 | Liu et al. .................... | 351/206 |
| 2003/0071968 A1 | 4/2003 | Lai et al. ..................... | 351/212 |
| 2006/0170866 A1* | 8/2006 | Mohr et al. .................. | 351/206 |

FOREIGN PATENT DOCUMENTS

| | | |
|---|---|---|
| EP | 1 138 254 A1 | 10/2001 |
| EP | 1 138 257 A1 | 10/2001 |
| WO | WO 03/032823 A2 | 4/2003 |

OTHER PUBLICATIONS

German Patent Office Search Report for Application No. DE 203 13 745.0, 3 pgs. (Nov. 5, 2004).
European Patent Office Search Report for Application No. EP 04015868.5-1265, 3 pgs. (Nov. 23, 2004).

* cited by examiner

*Primary Examiner*—Hung Dang
*Assistant Examiner*—Mohammed Hasan
(74) *Attorney, Agent, or Firm*—Blakely, Sokoloff, Taylor & Zafman LLP

(57) ABSTRACT

Ophthalmologic analysis system for measuring the thickness of the corneal tissue on an eye to be examined having a projection device with which defined regions of the corneal tissue are illuminated, whereby the projection device cooperates with an observation system by means of which the illuminated regions of the corneal tissue can be observed and recorded at an angle in relation to the beam path of the projection device. A second projection device is provided on the analysis system, whereby the second projection device cooperates with a second observation system by means of which the illuminated regions of the corneal tissue are observed and recorded such that the curvature of the corneal tissue can be derived from the image information of the second observation system in the analysis device.

21 Claims, 6 Drawing Sheets

OPHTHALMOLOGIC ANALYSIS SYSTEM

FIELD

This invention relates to an ophthalmologic analysis system for measuring the thickness of the cornea on the human eye according to the preamble of claim 1.

BACKGROUND

Such analysis systems are of major importance in ophthalmology. By using suitable image processing methods, the significant properties of the corneal tissue can be ascertained extremely effectively.

Tests have shown that the measurement of the thickness of the cornea depends on the radius of curvature of the cornea in the measurement range. In other words, this means that the means known so far for measuring the thickness of the corneal tissue have been subject to a measurement error, with the deviation being greater, the greater the difference between the actual curvature of the cornea in the measurement range and the reference value preselected in the analysis system. Against the background of this state of the art, the object of the present invention is therefore to make available an ophthalmologic analysis system with which this measurement accuracy can be increased.

SUMMARY

This object is achieved by an analysis system according to the teaching of claim 1.

Advantageous embodiments of this invention are the object of the subclaims.

This invention is based on the basic idea of combining in one instrument the known pachymetric analysis systems with another analysis system with which the curvature of the cornea can be measured. As a result, it is possible in a single examination of the patient using one instrument to determine both the thickness and curvature of the cornea.

The curvature of the corneal tissue may also be used in deriving the measured value for the thickness of the cornea from the image information, so that measurement errors in the derivation of the thickness of the corneal tissue due to deviations in the assumed curvature of the corneal tissue can be ruled out.

The first projection device for examination of the cornea may preferably be designed in the manner of slit lighting. Lighting of the corneal tissue with a light slit has proven most suitable for measuring the thickness of the cornea.

In addition, it is especially advantageous if the beam path of the slit lighting is deflected at least once by 90° on a reflector element, in particular by 90° on each of two reflector elements. This makes it possible to implement a very compact instrument design because the beam path of the slit lighting can be folded through appropriate deflection.

A stationary arrangement of the slit lighting ensures an extremely accurate adjustment of the slit diaphragm so that measurement errors due to unwanted deviations in the slit diaphragm are ruled out.

A particularly great image resolution of the image data obtained by the first observation system is achieved when a Scheimpflug system is imaged through an appropriate arrangement with intermediate angles from the first projection device and from the first observation system.

It is essentially irrelevant how the curvature of the corneal tissue is measured. According to a first embodiment, it is conceivable to use a topographic measurement system for measuring the topography of the cornea. Such topographic measurement systems are known in the state of the art and are suitable in principle for measuring the curvature of the corneal tissue in all parts of the cornea.

According to a second embodiment, the second projection device, the second observation system and the analysis device together form a keratometer.

To measure the curvature of the cornea with a keratometer, a defined measurement mark may be projected onto the cornea and the distortion in the measurement mark occurring due to curvature is measured on the cornea. A combination of two collimated light spots and an essentially circular light strip which is not collimated is especially suitable for use as the measurement mark.

Two tubes that are cylindrical, for example, may be provided on the keratometer to produce the collimated light spots. A light-emitting diode (LED) is provided as the lighting means in the interior of these tubes, with at least one lens being positioned in front of the LED to create the collimated light.

To produce the circular non-collimated light strip, a circular cylindrical light guide element may be used. The light is input on the end face and/or on the circumference of the cylinder by lighting with a lighting means on the back side of the light guide element, e.g., a strip of plastic that conducts light. The light then leaves the light guide element on the forward end face and is projected onto the cornea as a circular non-collimated light strip according to the circular cylindrical shape of the light guide element. LEDs in particular may be used as the lighting means for input of the light into the light guide element.

To facilitate processing and/or storing of the image data observed by the first observation system and/or the second observation system, it is particularly advantageous if suitable video sensors are used for image pickup, these sensors optionally relaying the image data in the form of a video signal to downstream function units, e.g., an image processing system.

To permit digital image processing, the video signal should preferably be generated in a digital data format or, if the image data is recorded in analog form, the video signal should be converted to a digital data format.

For calculating the thickness of the corneal tissue and/or the curvature of the corneal tissue from the image data thus recorded, preferably a digital signal processing system should be used, such as that installed on a standard PC, for example.

In particular so-called chip cameras, e.g., CMOS chips or CCD chips have proven successful as video sensors.

To measure the thickness of the corneal tissue, the eye to be examined must be aligned as accurately as possible in relation to the observation optics. Using the video sensor of the second observation system, which is used itself to measure the curvature of the cornea, as a setup camera makes it possible to eliminate the need for a separate setup camera.

The function units provided on the inventive analysis system also make it possible to use this system simultaneously as a pupillometer for measuring the pupil response as a function of time. Apart from the image processing software which is suitable here accordingly, no additional optical function units are needed to perform pupillometry.

The pupil position could also be used in particular to determine the point of intersection, i.e., the relative position of the eye to be examined in relation to the instrument. In this manner, the pupillometer may also be used as a centering system for positioning the eye to be examined.

It is particularly advantageous if the analysis system is accommodated in a housing which can be connected to an instrument mount. In this way, it is not necessary to have an independent instrument mount for positioning the analysis system in front of the eye to be examined. Instead of this, a standard instrument mount such as that available anyway in many ophthalmology practices is used for this purpose.

BRIEF DESCRIPTION OF THE DRAWINGS

One embodiment of this invention is diagramed schematically in the drawings and explained below with examples.

DETAILED DESCRIPTION

Figure 1:
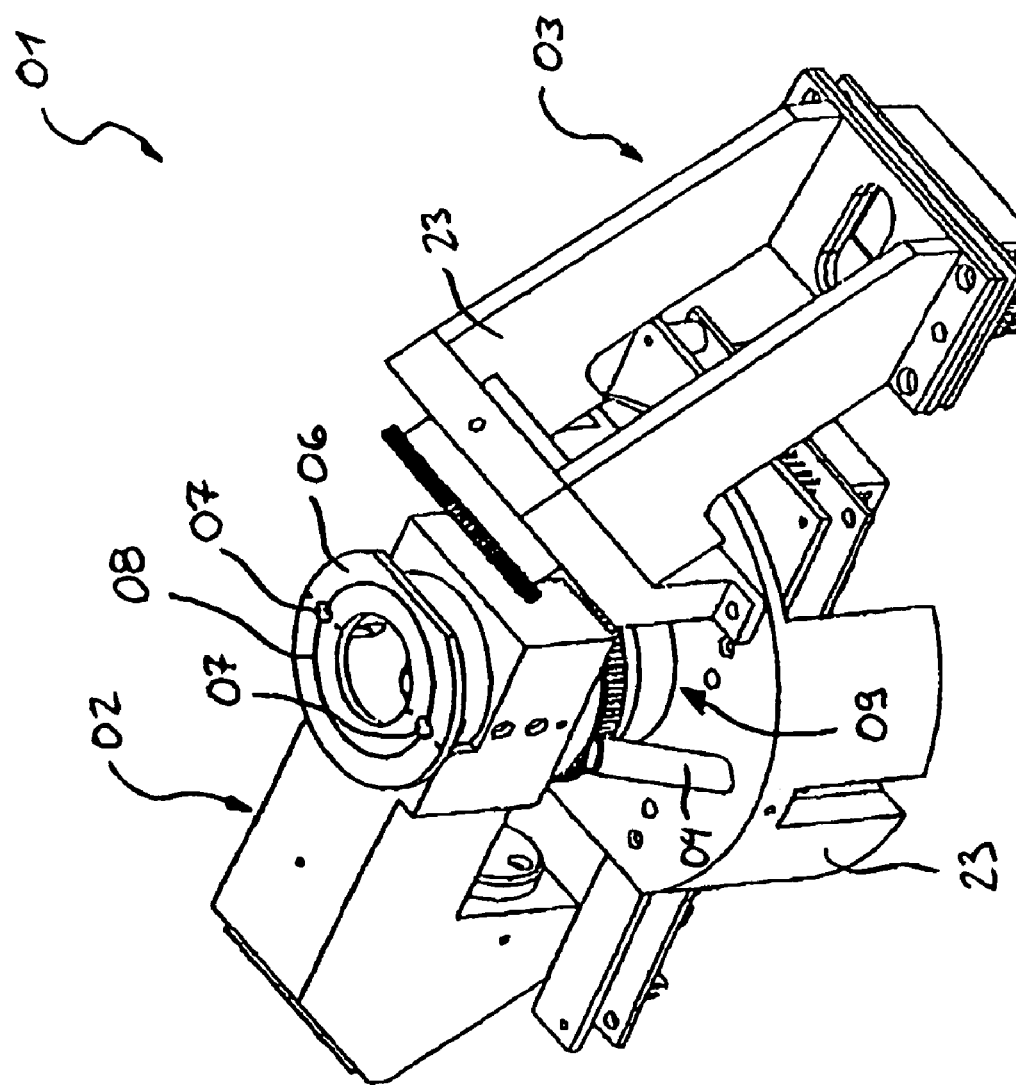
FIG. 1 shows an ophthalmologic analysis system in a perspective view.
Figure 2:
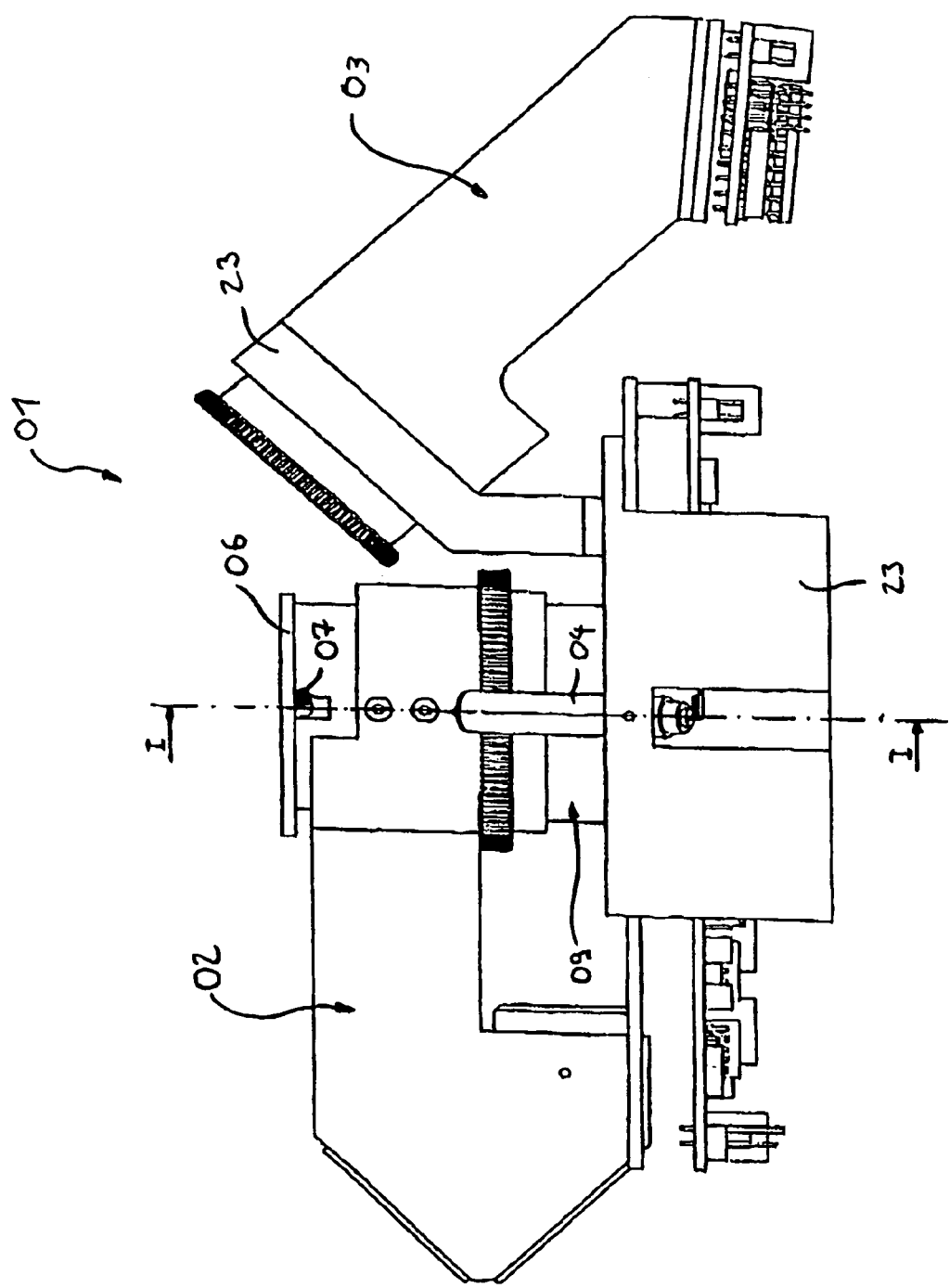
FIG. 2 shows the analysis system according to FIG. 1 in a side view.

FIG. 1 illustrates an ophthalmologic analysis system 01 for combined examination of a patient's eyes, shown here in perspective view. The analysis system 01 is installed in a housing 23, which is composed of multiple parts and has various accessory parts and can be connected to a suitable instrument mount (not shown here).

For one type of examination in which the thickness of the corneal tissue of the eye A is measured, a first projection device 02 designed in the manner of a slit lighting is provided. The function of the first projection device 02 is explained in greater detail below. The measurement system for measuring the thickness of the cornea is completed by a first observation system 03 which is designed in the manner of Scheimpflug camera system.

The keratometric measurement system for measuring the curvature of the corneal tissue has a projection device with which two collimated spots of light and an essentially circular non-collimated strip of light can be projected onto the eye A. To create the collimated light spots, two tubes 04 and 05 are provided, directed at the point of intersection of the different beam axes, an LED 10 generating a collimated light beam in the interior of these tubes in cooperation with a lens 11. The two light beams pass through a lens ring 06 in two recesses 07 provided for this purpose and are projected in this way onto the eye A to be examined. The circular non-collimated light strip is created by a circular cylindrical light guide element 08. The light guide element 08 is illuminated on its rear side with LEDs 12, so that the light input into the light guide element 08 opposite the eye A to be examined can emerge on the forward end face in the form of a circular strip of light. The keratometric measurement system is completed by a second observation system 09.

Figure 3:
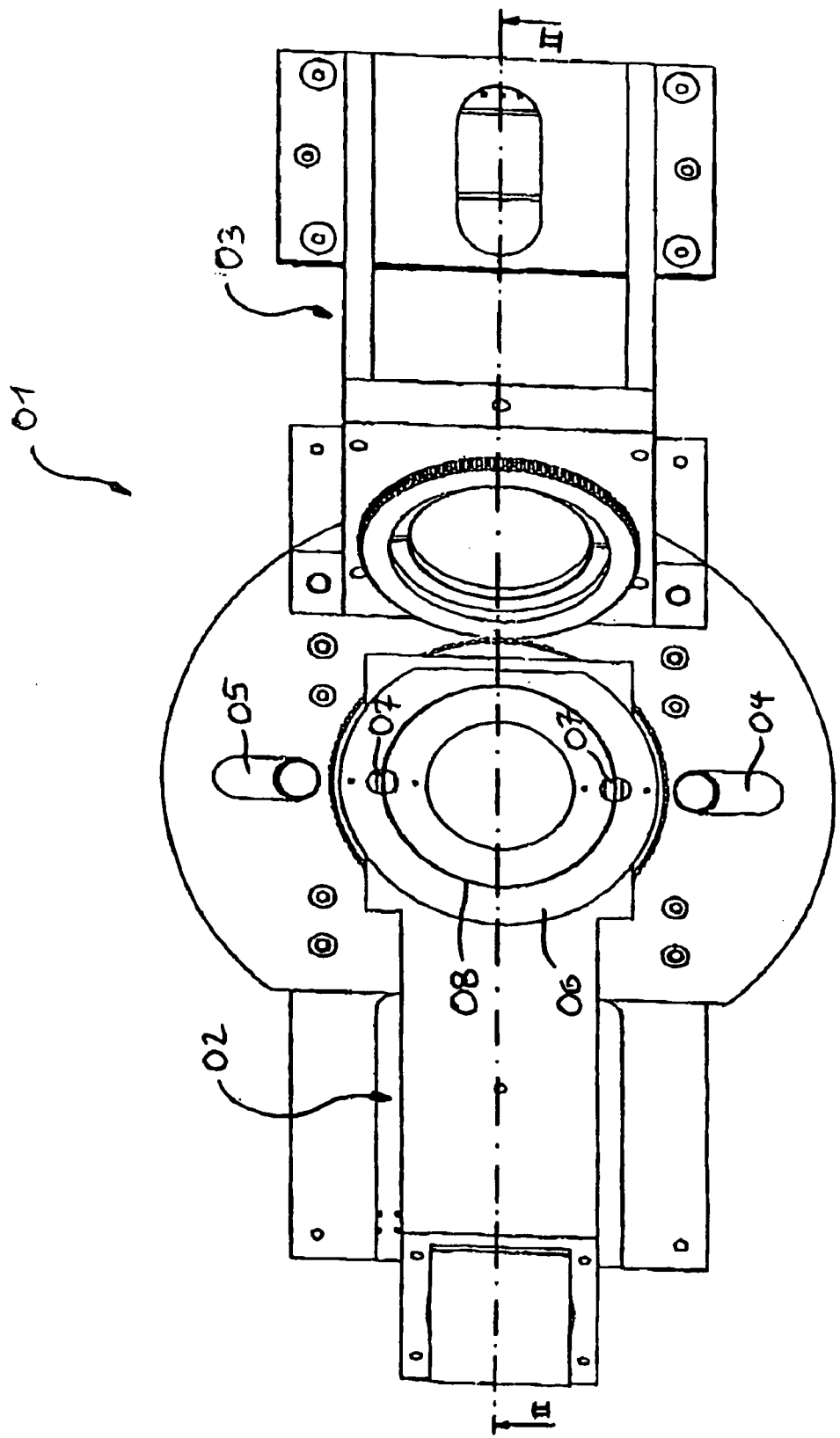
FIG. 3 shows the analysis system according to FIG. 1 in a view from above.
Figure 4:
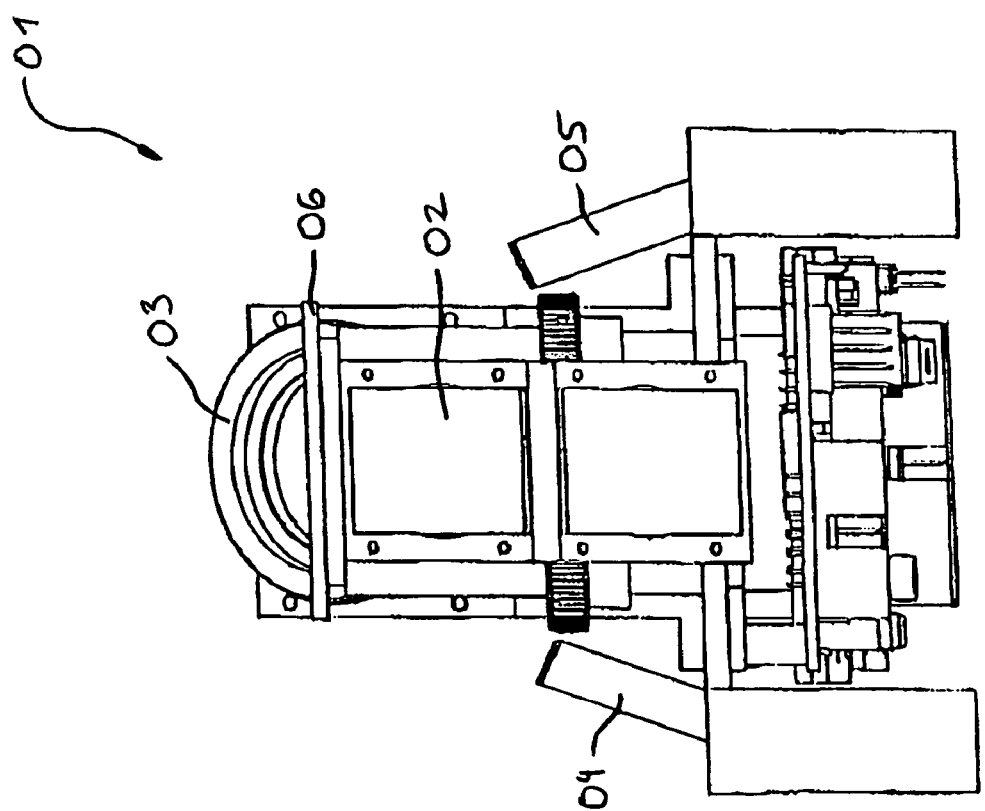
FIG. 4 shows the analysis system according to FIG. 1 in a view from the front.

FIG. 1, FIG. 3 and FIG. 4 show the analysis system 01 in various views from different angles.

Figure 5:
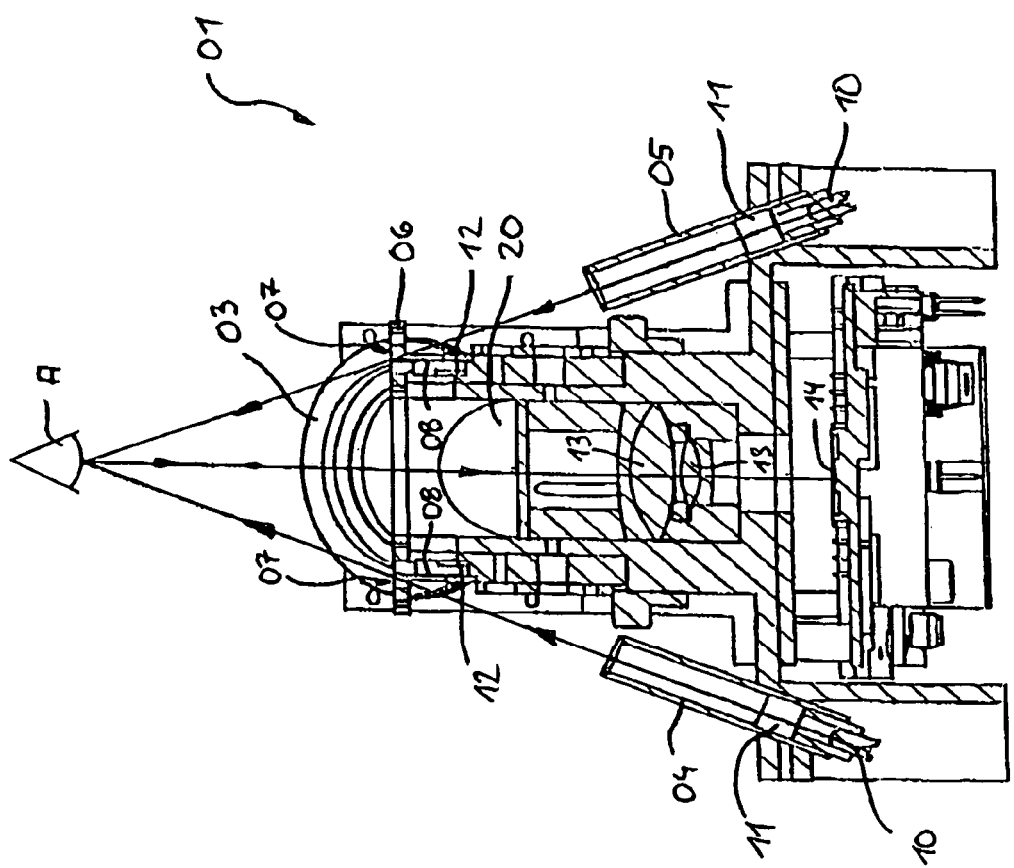
FIG. 5 shows the analysis system according to FIG. 1 in a cross section along line sectional line I-I.
Figure 6:
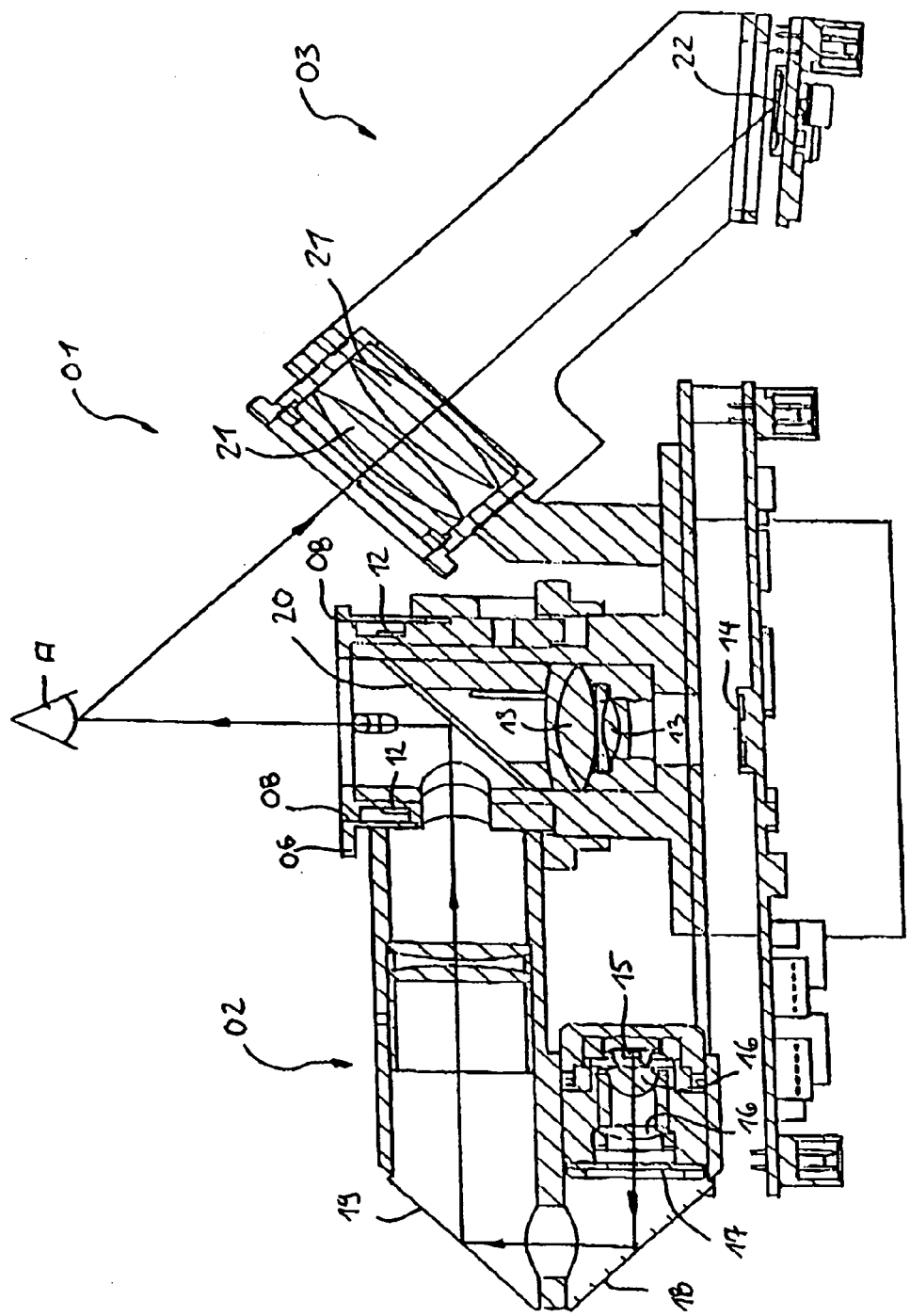
FIG. 6 shows the analysis system according to FIG. 1 in a longitudinal section along sectional line II-II.

On the basis of the cross section shown in FIG. 5, the functioning of the keratometric measurement system will now be explained briefly. An LED 10 is provided in each of tubes 04 and 05, a lens 11 being situated upstream from each LED. In this way, collimated light beams are created in the tubes 04 and 05 and are projected through the recesses 07 in the lens ring 06 onto the eye A to be examined. To generate the circular ring-shaped non-collimated strip of light, a light guide element 08 shaped in the form of a circular cylinder is inserted into the lens ring 06 in such a way that the forward end face of the light guide element 08 is sealed with the outside of the lens ring 06. Several light emitting diodes 12 are provided on the rear side of the light guide element 08, these LEDs being uniformly distributed over the circumference of the light guide element 08. The light emitted by the LEDs 12 is input into the light guide element 08 on the inside circumference and emerges again as a circular non-collimated strip of light on the forward end face of the light guide element 08.

The light mark generated jointly by the tubes 04 and 05 and the light guide element 08 is projected onto the eye A that is to be examined. The light mark is imaged on the cornea and is observed through the observation system 09, which has multiple lenses 13 and a chip camera 14. The image data recorded by the chip camera 14 is processed digitally and relayed to a digital image processing system. In the image processing system the image data is analyzed in a manner suitable for calculating the radius of curvature of the cornea from the image data.

The function of the measurement system for measuring the thickness of the cornea with the projection device 02 and the observation system 03 is diagramed schematically in the longitudinal section according to FIG. 7. An LED 15 with two lenses 16 positioned in front of it serves as the lighting means for the slit lighting in the projection device 02. To generate the slit light, a slit diaphragm 17 containing a narrow light slit is provided. Then the light beam is deflected by 90° on each of two reflectors 18 and 19 and is projected by a partially mirrorized reflector element 20 onto the eye A that is to be examined. The light slit projected on to the eye A is imaged by the lenses 21 on a chip camera 22, so that the digital image data recorded there can be analyzed in a digital processing system to derive the thickness of the cornea.

What is claimed is:

1. An ophthalmologic analysis system (01) for measuring the thickness of the corneal tissue on an eye (A) that is to be examined, having a projection device (02) with which defined regions of the corneal tissue are illuminated, whereby the projection device (02) cooperates with an observation system (03) through which the illuminated area of the corneal tissue is observed and recorded at an angle relative to the beam path of the projection device (02) such that the thickness of the corneal tissue can be derived in an analysis device from the image information of the observation system (03), the ophthalmologic analysis system comprising:

a second projection device (04, 05, 08) is provided on the analysis system (01) with which defined regions of the corneal tissue are illuminated, whereby the second projection device (04, 05, 08) cooperates with a second observation system (09) through which the illuminated regions of the corneal tissue are observed and recorded, such that the curvature of the corneal tissue can be derived from the image information of the second observation system (09) in the analysis device.

2. The analysis system according to claim 1, wherein the first projection device (02) is designed in the manner of slit lighting, so that the corneal tissue can be illuminated with a light slit.

3. The analysis system according to claim 2, wherein the beam path of the slit lighting (02) is deflected by 90° at least once on a reflector element (18, 19), in particular being deflected by 90° each time on two reflector elements (18, 19).

4. The analysis system according to claim 2, wherein the slit lighting (02) is arranged to be stationary.

5. The analysis system according to claim 2, wherein one or more LEDs (15) are used as the lighting means for the first projection device (02).

6. The analysis system according to claim 2, wherein the beam path of the first projection device (02), the beam path of the first observation system (03) and the projection plane (22) of the first observation system (03) are arranged with intermediate angles so that the first projection device (02) and the first observation system (03) together form a Scheimpflug system.

7. The analysis system according to claim 1, wherein the second projection device, the second observation system and the analysis device together form a topographic measurement system for measuring the topography of the cornea.

8. The analysis system according to claim 1, wherein the second projection device (04, 05, 08), the second observation system (09) and the analysis device together form a keratometer.

9. The analysis system according to claim 8, wherein a defined measurement mark can be projected onto the cornea with the projection device (04, 05, 08) of the keratometer.

10. The analysis system according to claim 9, wherein the measurement mark has two collimated light spots and a non-collimated light strip that is essentially circular.

11. The analysis system according to claim 10, wherein the collimated light spots are each produced by an LED (10) arranged in a tube (04, 05) with at least one lens (11) in front of the light-emitting diode.

12. The analysis system according to claim 10, wherein the circular non-collimated light strip is created by a circular cylindrical light guide element (08) whereby the light of at least one lighting means (15) is input into the light guide element on the rear end face and/or on the circumference of the cylinder and emerges from the light guide element (08) on the forward end face.

13. The analysis system according to claim 12, wherein several LEDs (12) distributed around the circumference of the circular cylindrical light guide element (08) serve as the lighting means.

14. The analysis system according to claim 1, wherein at least one video sensor (14, 22) is provided in the first observation system (03) and/or in the second observation system (09) so that the cornea can be observed and recorded, with the video sensor (14, 22) relaying the image data in the form of a video signal.

15. The analysis system according to claim 14, wherein the video signal is generated in a digital data format or is converted to a digital data format.

16. The analysis system according to claim 15, wherein a digital image processing system is provided as the analysis device, with which the thickness of the corneal tissue and/or the curvature of the corneal tissue can be derived from the digital image data.

17. The analysis system according to claim 14, wherein the video sensor is designed in the manner of chip camera (14, 22).

18. The analysis system according to claim 14, wherein the video sensor (14) of the second observation system (09) can be used as a setup camera for aligning the eye (A) that is to be examined in the correct position.

19. The analysis system according to claim 1, wherein the analysis system (01) can be used as a pupillometer.

20. The analysis system according to claim 19, wherein the pupillometer can be used as a centering system for positioning the eye (A) to be examined.

21. The analysis system according to claim 1, wherein the analysis system (01) is accommodated in a housing (23) which can be connected to an instrument mount.

* * * * *